United States Patent
Moynihan et al.

(10) Patent No.: US 6,365,349 B1
(45) Date of Patent: Apr. 2, 2002

(54) APPARATUS AND METHODS FOR ARRAYING SOLUTION ONTO A SOLID SUPPORT

(75) Inventors: Kristen Moynihan; Jeffrey Van Ness, both of Seattle; John C. Tabone, Bothell, all of WA (US)

(73) Assignee: Qiagen Genomics, Inc., Bothell, WA (US)

( * ) Notice: Subject to any disclaimer, the term of this patent is extended or adjusted under 35 U.S.C. 154(b) by 0 days.

(21) Appl. No.: 09/120,689

(22) Filed: Jul. 21, 1998

Related U.S. Application Data (60) Provisional application No. 60/053,435, filed on Jul. 22, 1997.

(51) Int. Cl.[7] .............................. C12Q 1/68; C12M 1/34; C07H 21/02

(52) U.S. Cl. .................. 435/6; 435/287.2; 536/23.1

(58) Field of Search ...................... 29/846, 825; 439/66; 435/6, 91.1, 91.2, 183, 287.2; 436/94; 536/23.1, 24.3, 24.31, 24.33

(56) References Cited

U.S. PATENT DOCUMENTS

| | | | |
|---|---|---|---|
| 4,020,698 A | 5/1977 | D'Autry | 73/425.6 |
| 4,753,983 A | 6/1988 | Ngo | 525/54.1 |
| 4,827,780 A | 5/1989 | Sarrine et al. | 73/864.21 |
| 4,981,783 A | 1/1991 | Augenlicht | 435/6 |
| 4,983,909 A | 1/1991 | Swart et al. | 324/158 |
| 5,143,854 A | 9/1992 | Pirrung et al. | 436/518 |
| 5,250,613 A | 10/1993 | Bergstrom et al. | 525/54.1 |
| 5,384,261 A | 1/1995 | Winkler et al. | 436/518 |
| 5,436,327 A | 7/1995 | Southern et al. | 536/25.34 |
| 5,474,796 A | 12/1995 | Brennan | 427/2.13 |
| 5,500,339 A | 3/1996 | Fuller et al. | 435/6 |

(List continued on next page.)

FOREIGN PATENT DOCUMENTS

| | | |
|---|---|---|
| CA | 2214430 | 9/1996 |
| DE | 28 52 886 | 6/1980 |
| DE | 197 42 227 A1 | 4/1999 |
| EP | 197 784 A1 | 10/1985 |
| EP | 403 700 A1 | 12/1990 |
| EP | 649 909 A2 | 4/1995 |
| EP | 785 280 A2 | 7/1997 |
| GB | 2 197 720 A | 5/1988 |
| WO | WO 94/03643 | 2/1794 |
| WO | WO 85/04720 | 10/1985 |
| WO | WO 90/13666 | 11/1990 |
| WO | WO 91/04266 | 4/1991 |
| WO | WO 91/07505 | 5/1991 |

(List continued on next page.)

OTHER PUBLICATIONS

Blanchard et al., (1996), "High–density oligonucleoyide arrays," *Biosens. Bioelectron. 11*: 687–690.

Chee et al., (1996), "Accessing genetic information with high–density DNA arrays," *Science 274*: 610–614.

Chu et al., (1998), "The transcriptional program of sporulation in budding yeast," *Science 282*, 699–705.

(List continued on next page.)

*Primary Examiner*—Bradley L. Sisson
(74) *Attorney, Agent, or Firm*—SEED Intellectual Property Law Group PLLC (57) ABSTRACT

A method for depositing biomolecule onto a solid support, the method including the steps of: immersing a tip of a spring probe into a solution of biomolecule; removing said tip from said solution to provide biomolecule solution adhered to said tip; and contacting said biomolecule solution with a solid support to thereby transfer biomolecule solution from said tip to said solid support. The spring probe has a planar tip but it otherwise identical to commercial spring probes. The solution of biomolecule contains a thickening agent in addition to biomolecule, where oligonucleotide is a preferred biomolecule.

23 Claims, 7 Drawing Sheets

U.S. PATENT DOCUMENTS

| | | | |
|---|---|---|---|
| 5,514,785 A | 5/1996 | Van Ness et al. | 536/22.1 |
| 5,525,464 A | 6/1996 | Drmanac et al. | 435/6 |
| 5,551,487 A | 9/1996 | Gordon et al. | 141/1 |
| 5,557,213 A | 9/1996 | Reuter et al. | 324/761 |
| 5,600,883 A * | 2/1997 | Faure et al. | 29/846 |
| 5,641,658 A | 6/1997 | Adams et al. | 435/91.2 |
| 5,658,802 A | 8/1997 | Hayes et al. | 436/518 |
| 5,709,668 A | 1/1998 | Wacks | 604/232 |
| 5,718,040 A * | 2/1998 | Faure et al. | 29/846 |
| 5,741,554 A | 4/1998 | Tisone | 427/424 |
| 5,744,305 A | 4/1998 | Fodor et al. | 435/6 |
| 5,756,050 A | 5/1998 | Ershow et al. | 422/100 |
| 5,770,151 A | 6/1998 | Roach et al. | 422/63 |
| 5,770,367 A | 6/1998 | Southern et al. | 435/6 |
| 5,800,992 A | 9/1998 | Fodor et al. | 435/6 |
| 5,807,522 A | 9/1998 | Brown et al. | 422/50 |
| 5,814,502 A | 9/1998 | Hoeltke et al. | 435/188 |
| 5,837,860 A | 11/1998 | Anderson et al. | 536/25.3 |
| 5,919,523 A | 7/1999 | Sundberg et al. | 427/333 |
| 6,101,946 A | 8/2000 | Martinsky | 101/494 |

FOREIGN PATENT DOCUMENTS

| | | |
|---|---|---|
| WO | WO 92/07006 | 4/1992 |
| WO | WO 93/19207 | 9/1993 |
| WO | WO 94/00600 | 1/1994 |
| WO | WO 94/11388 | 5/1994 |
| WO | WO 94/29484 | 12/1994 |
| WO | WO 95/02184 | 1/1995 |
| WO | WO 95/04594 | 2/1995 |
| WO | WO 95/09248 | 4/1995 |
| WO | WO 95/20679 | 8/1995 |
| WO | WO 95/25116 | 9/1995 |
| WO | WO 95/33073 | 12/1995 |
| WO | WO 95/35505 | 12/1995 |
| WO | WO 96/04404 | 2/1996 |
| WO | WO 96/27680 | 9/1996 |
| WO | WO 96/31622 | 10/1996 |
| WO | WO 98/14271 | 4/1998 |
| WO | WO 99/04896 | 2/1999 |
| WO | WO 99/05308 | 2/1999 |
| WO | WO 99/15543 | 1/2000 |

OTHER PUBLICATIONS

Cronin et al., (1996), "Cystic Fibrosis Mutation Detection by Hybridization to Light–Generated DNA Probe Arrays," *Human Mutation* 7:244–255.

DeRisi et al., (1996), "Use of a cDNA microarray to analyze gene expression patterns in human cancer," *Nat Genet 14*: 457–460.

DeRisi et al., (1997), "Exploring the metabolic and genetic control of gene expression on a genomic scale," *Science* 278: 680–686.

de Saizieu et al., (1998), "Bacterial transcript imaging by hybridization of total RNA to oligonucleotide arrays," *Nature Biotech. 16*: 45–48.

Drmanac et al., (1998), "Accurate sequencing by hybridization for DNA diagnostics and individual genomics," *Nature Biotech. 16*: 54–58.

Fodor et al., (1991), "Light–directed, spatially addressable parallel chemical synthesis," *Science 251*: 767–773.

Hacia et al., (1996), "Detection of heterozygous mutations in BRCA1 using high density oligonucleotide arrays and two–colour fluorescence analysis," *Nature Genet. 14*: 441–447.

Heller et al., (1997), "Discovery and analysis of inflammatory disease–related genes using cDNA microarrays," *Proc Natl Acad Sci USA*. 94:2150–2155.

Khrapko et al., (1991), "Hybridization of DNA with oligonucleotides immobilized in gel: a convenient method for detecting single base substitutions," *Molecular Biology 25*: 581–591.

Kozal et al., (1996), "Extensive polymorphisms observed in HIV–1 clade B protease gene using high–density oligonucleotide arrays," *Nature Med. 2*: 753–759.

Lashkari et al., (1997), "Yeast microarrays for genome wide parallel genetic and gene expression analysis," *Proc. Natl. Acad. Sci. USA 94*: 13057–13062.

Lemieux et al., (1998) "Overview of DNA Chip Technology," *Molecular Breeding 4*: 277–289.

Lockhart et al., (1996), "Expression Monitoring by Hybridization to High–Density Oligonucleotide Arrays," *Nature Biotechnology 14*: 1675–1680.

Maier et al., (1994), "Application of robotic technology to automated sequence fingerprint analysis by oligonucleotide hybridisation," Summary.

Pease et al., (1994), "Light–generated oligonucleotide arrays for rapid DNA sequence analysis," *Proc. Natl. Acad. Sci. USA 91*: 5022–5026.

Sapolsky and Lipshutz, (1996), "Mapping Genomic Library Clones Using Oligonucleotide Arrays," *Genomics 33*: 445–456.

Schena et al., (1995), "Quantitative monitoring of gene expression patterns with a complementary DNA microarray," *Science 270*:467–470.

Schena, M., (1996), "Genome Analysis with Gene Expression Microarrays," BioEssays 18: 427–431.

Schena et al., (1996), "Parallel human genome analysis: microarray–based expression montitoring of 1000 gene," *Proc Natl Acad Sci USA93*: 10614–10619.

Schena et al., (1998), "Microarrays: Biotechnology's discovery platform for functional genomics," *Trends Biotech. 16*: 301–306.

Schena and Davis, (1998), "Parallel Analysis with Biological Chips. in PCR Methods Manual," Academic Press (San Diego), in press.

Shalon et al., (1996), "A DNA micro–array system for analyzing complex DNA samples using two–color fluorescent probe hybridization," *Genome Research 6*: 639–645.

Shoemaker et al., (1996), "Quantitative phenotypic analysis of yeast deletion mutants using a highly parallel molecular bar–coding strategy," *Nature Genetics 14*: 450–456.

Wodicka et al., (1997), "Genome–wide expression monitoring in *Saccharomyces cerevisiae*," *Nature Biotech. 15*: 1359–1367.

Yershov et al. (1996), "DNA analysis and diagnostics on oligonucleotide microchips," *Proc. Natl. Acad. Sci. USA 93*: 4913–4918.

http://cmgm.stanford.edu/pbrown/mguide, Sep. 12, 2000 and http://cmgm.stanford.edu/pbrown/mguide/tips.html, Sep. 12, 2000.

Schummer et al., "Inexpensive Handheld Device for the Construction of High–Density Nucleic Acid Arrays," *Biotechniques 23*(6): 1087–1092, 1997.

Hamilton Microlab Arrayer, modular print head, http://chroma.mbt.washington.edu/mod_www/array.html.[Accessed Nov. 19, 1998].

* cited by examiner

APPARATUS AND METHODS FOR ARRAYING SOLUTION ONTO A SOLID SUPPORT

CROSS-REFERENCE TO RELATED APPLICATION

The present application claims the benefit of U.S. Provisional Patent Application No. 60/053,435, filed Jul. 22, 1997.

TECHNICAL FIELD

This invention relates to microfabrication technology, such as DNA chip-making technology, and more specifically to methods and apparatuses for delivering controlled amounts of a solution to specific, closely spaced locations on a solid support.

BACKGROUND OF THE INVENTION

In the fields of molecular biology and microbiology it has long been common in the art to make replicate arrays of biological agents to facilitate parallel testing of many samples. For example, the use of sterile velvet cloths and a piston-ring apparatus has long been used to make replicate agar plates of bacterial and yeast colonies on many plates, each containing a different growth medium, as a way of rapidly screening a large number of independent colonies for different growth phenotypes (Lederberg and Lederberg, J. Bacteriol. 63:399, 1952). Likewise, 96-well microtiter plates have long been used to store, in an organized and easily accessed fashion, large numbers of cell lines and virus isolates representing recombinant DNA libraries or monoclonal antibody cell lines.

Experimental screening of the 96-well microtiter plates housing a clone collection is commonly accomplished by using a rigid metal or plastic 96-pin device designed so that each pin is spaced relative to the others such that it fits precisely into the microtiter plate. Depending on the task at hand, the 96-pin device is lowered carefully to the surface of an nutrient-agar plate (if the objective was to grow replicate biological samples), into another microtiter plate (to grow or dilute the samples), onto nylon embranes (for molecular screening by DNA or RNA hybridization to identify a particular recombinant clone), or transferred for use in any other screening or procedure that is adaptable to the 96-well microtiter dish format.

While multiple prints may be performed from one pin dip into the samples arrayed in the master microtiter dish, the amount of sample deposited during each sequential print drops off. The ability to control the uptake of a solution onto the printing pin, and the deposition of solution onto a printing surface are critical to realizing an aliquotting devise which meets the technical needs of microarray production for the fields of genomics, molecular biology and molecular diagnostics.

An important factor in developing a successful printing process is the ability to control the force and speed of movement with which the pin tips contacts the surface being printing upon. As noted by Drmanac and Drmanac (BioTechniques 17:328, 335, 1994), two problems with conventional flat-cylinder pins are that drops can be caught on the sides of a pin leading to irregular printing, and drop splashing can occur when the printing pin head is withdrawn too fast from the printing surface. Too much force can lead to extensive damage to the print surface negating the utility of that print array. Too little force may be just as disabling in that variable amounts of sample may be transferred, or the print maybe defective all together. For example, when printing bacterial or viral samples to the surface of a nutrient-agar plate, too much pressure results in disruption of the agar surface, while too little force may result in little or no transfer of a sample. In addition, many nucleic acid hybridization membrane surfaces are fragile and are easily damaged by excess pin head force during sample printing.

The advent of large scale genomic projects and the increasing medical use of molecular diagnostics, has prompted the development of large volume throughput methods for screening recombinant DNA libraries representing entire genomes, the performance of large scale DNA sequencing projects, and executing replicative immunological assays, nucleic acid hybridization assays, or polymerase chain reaction assays. The following publications (and the references cited therein), which are exemplary only, provide general and specific overviews of large throughput methods that rely on biomolecular arrays, as well as methods of preparing such arrays: Eggers, M. D. et al. Advances in DNA Sequencing Technology SPIE Vol. 1891:113–126, 1993; Chetverin, A. B. et al. Bio/Technology 12:1093–1099, 1994; Southern, E. M. Nucleic Acids Research 22:1368–1373, 1994; Lipshutz, R. J. et al. BioTechniques 19:442–447, 1995; Schena, M. BioEssays 18:427–431, 1996; Blanchard, A. P. et al. Biosensors & Bioelectronics 11:687–690, 1996; O'Donnell-Maloney, M. J. et al. Genetic Analysis: Biomolecular Engineering 13:151–157, 1996; Regalado, A. Start-Up 24–30, October 1996; and Stipp, D. Fortune pp. 30–41, Mar. 31, 1997.

The need for high throughput methodology has led, in some cases, to a change from a 96-well microtiter dish format, to a 384-well (Maier et al., J. Biotechnology 35:191, 1994) or 864-well (Drmanac et al., Electrophoresis 13:120, 1992) format, which can also be used in conjunction with robotic devises (see, e.g., Belgrader et al., BioTechniques 19:426, 1995; Wilke et al., Diagnostic Microbiology and Infect. Disease 21:181, 1995). However, all of these automated techniques require the use of a robotic pin-tool devise that is capable of reproducibly transferring equal volumes of liquid from one arrayed configuration (i.e., 96-well microtiter plate) to another (i.e., 96-spot array on a hybridization filter membrane).

Recently, methods have also been developed to synthesize large arrays of short oligodeoxynucleotides (ODNs) bound to a glass surface that represent all, or a subset of all, possible nucleotide sequences (Maskos and Southern, Nucl. Acids Res. 20: 1675, 1992). Once such an ODN array has been made may be used to perform DNA sequencing by hybridization (Southern et al., Genomics 13:1008, 1992; Drmanac et al., Science 260:1649, 1993). The utility of this method of DNA sequencing would be greatly improved if better methods existed for the transfer and arraying of the precise amounts of the biochemical reagents required for the synthesis of large sets ODNs bound to hybridizable surfaces. This would enable greater equality of ODN yield at each position within the array and also increase the nucleotide chain length it is possible to synthesize.

The polymerase chain reaction (PCR) has found wide application to many different biological problems. Two major limitations to the commercial utilization of PCR are the high cost of the reagents and the inability to automate the performance of the process. Reagent costs can be lowered if the total volume of each reaction can be decreased, allowing a concomitant decrease in DNA polymerase and nucleotides. An accurate and reliable means to array small volumes of reagents using a robotically controlled pin tool could help solve both of these PCR problems.

As noted above, transfer devices have been in use for some time in the fields of microbiology and molecular biology. The types of devises which have been used can be roughly divided into two categories. Pressure devises (e.g., pumps and automatic pipettes), driven by positive and/or negative pressure, which deliver fixed aliquots of liquids sample via a pipette tip to a solid surface or into a microtiter well. Pipette arrays have been constructed that correspond to the standard 96-well microtiter dish format (Reek et al., *BioTechniques* 19:282, 1995). These devices are most accurate in the 5 µl and above volume range, but are generally ill-suited to smaller volume tasks.

Solid surface pin devises transfer liquids based upon pin surface area and the factors regulating liquid surface tension, and have been widely adopted because of their simplicity and ability to transfer small volumes of liquid. These rigid pin devises have been used for several years in robotic devises to print multiple copies of nucleic acid microdot arrays which are then used in hybridization reactions to measure gene expression.

Researchers have modified the traditional rigid microarray printing tip so that it contains a micro-channel which functions by capillary action to collect and hold liquid for subsequent printing to a glass surface (Schena et al., *Science* 270:467, 1995; Schena, *BioEssays* 18.427, 1996; Shalon et al., *Genome Res.* 6:639, 1996). Such a print head has been used to print PCR amplified cDNA inserts into micro-arrays using a robotic system. Small volume (2 µl per microdot) hybridization reactions were performed using this system to measure the differential expression of 45 genes by means of simultaneous, two color fluorescence hybridization (Schena et al., (*Science* 270:467, 1995).

There is a need in the art for highly efficient, cost effective means for arraying oligonucleotides and other biomolecules on a planar solid support. The present invention provides these and related advantages as disclosed in more detail herein.

SUMMARY OF THE INVENTION

In one aspect, the invention provides a spring probe comprising a tubular housing encasing a compression spring. The spring is in mechanical communication with a plunger. The plunger has a first region extending out of the housing, where the first region comprises a cone-shaped tip terminating in a flat surface. The flat surface is perpendicular to a longitudinal axis of the housing. The cone-shaped tip has, in cross-section, two exterior sides adjacent to the surface which, if the sides extended past the surface, would meet at a point positioned a distance of about 0.001–0.005 inches beyond the surface.

In another aspect, the invention provides a composition including a thickening agent at a concentration of about 35 vol % to about 80 vol % based on the total volume of the composition, an oligonucleotide at a concentration ranging from 0.001 µg/mL to 10 µg/mL, and water.

In another aspect, the invention provides a method for depositing a biomolecule onto a solid support. The method includes the steps of:

immersing a tip of a spring probe into a solution of biomolecule;

removing the tip from the solution to provide biomolecule solution adhered to the tip; and contacting the biomolecule solution with a solid support to thereby transfer biomolecule solution from the tip to the solid support.

The spring probe used in the depositing includes a tubular housing encasing a compression spring, as described above.

In another aspect, the invention provides a method for arraying a biomolecule. The method includes the steps of:

immersing a tip of a spring probe into a solution of biomolecule;

removing the tip from the solution to provide biomolecule solution adhered to the tip;

contacting the biomolecule solution with a solid support to thereby transfer biomolecule solution from the tip to the solid support; and repeating the contacting step a plurality of times to provide biomolecule patterned in an array on the solid support. Again, the spring probe having a tubular casing is as described above.

Other aspects of this invention will become apparent upon reference to the attached Figures and the following detailed description.

DETAILED DESCRIPTION OF THE INVENTION

The invention provides a method for depositing a biomolecule onto a solid support in a highly controlled manner, using a specially designed transfer device and/or specially formulated biomolecule solutions and/or specially coated solid supports. More specifically, the invention provides a method for depositing biomolecule onto a solid support, where the method includes the following steps:

immersing a tip of a spring probe into a solution of biomolecule;

removing said tip from said solution to provide biomolecule solution adhered to said tip; and contacting said biomolecule solution with a solid support to thereby transfer biomolecule solution from said tip to said solid support.

Spring probes have become generally well known since they were introduced early in the development of the printed circuit board industry. They are mechanical devices designed to meet the need for precision and reliability in the construction and testing of a variety of electronic components and their connections when being assembled into functioning circuit boards. Spring probes are essentially electro-mechanical devices, typically consisting of a tubular housing encasing a compression spring, ball and plunger. Some probes are specifically designed to carry electrical current flow, while others are used to drill, crimp, and secure components to a circuit board, and yet others are designed to perform soldering. There is nothing in the design or marketing of spring probes that suggests their potential utility as a mechanical devise for the transferring and arraying of solutions onto solid support for use in the fields of microbiology, biochemistry, or molecular biology.

Modified Spring Probes

Spring probes are available from several vendors including Everett Charles (Pomona, Calif.), Interconnect Devices Inc. (Kansas City, Kans.) and Test Connections Inc., (Upland, Calif.).

Figure 1A:
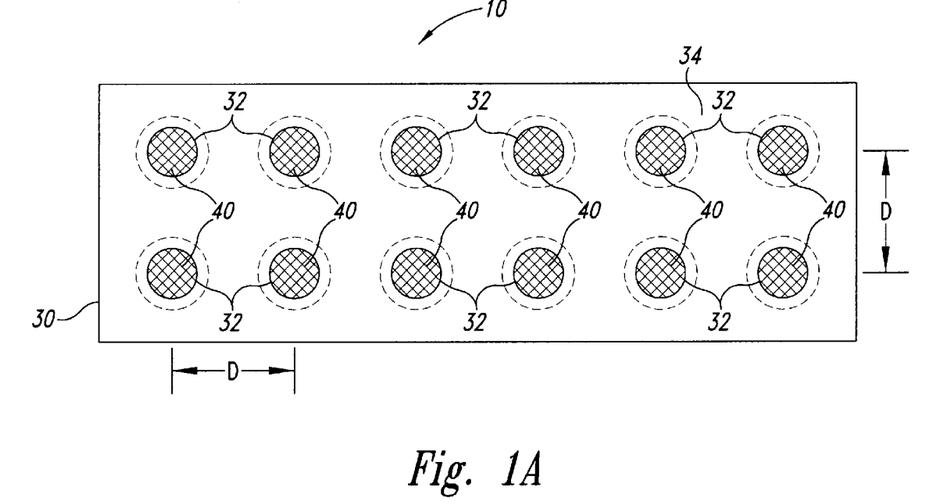
FIG. 1A is a schematic top plan view of an array in accordance with an embodiment of the invention.
Figure 2A:
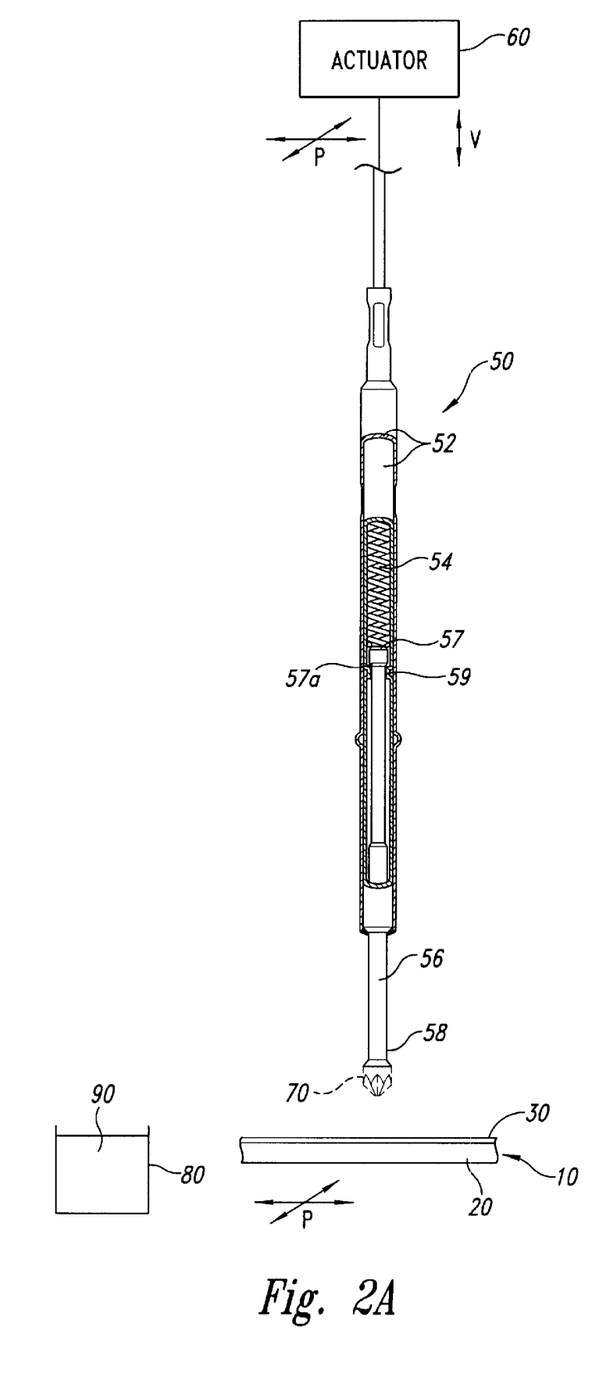
FIG. 2A is an isometric view of a delivery apparatus for preparing the arrays of the invention.

FIG. 2A is an isometric view showing a preferred apparatus and method for selectively delivering discrete, controlled volumes of a biomolecular solution onto the PEI layer 30 over the solid support 20 of the array 10. In one embodiment, the apparatus has a spring probe 50 operatively attached to an actuator 60 and a delivery tip 70 attached to an opposing end of the spring probe 50. The spring probe 50 generally includes a housing 52 encasing a biasing member 54 and a plunger 56 with a first end 57 adjacent to the biasing member 54 and a second end 58 projecting from the housing 52. The housing 52 may be a tubular barrel, and the biasing member 54 may be a compression spring that pushes the second end 58 of the plunger 56 out from the housing 52. The first end 57 of the plunger 56 according has a shoulder 57a that engages a stop 59 projecting radially inwardly from the housing 52 to limit the maximum extension of the plunger 56 with respect to the housing 52. Suitable spring probes 50 are available from Everett Charles (Pomona, Calif.), Interconnect Devices, Inc. (Kansas City, Kans.), Test Connections, Inc., (Upland, Calif.), and other manufacturers.

The actuator 60 preferably moves the spring probe 50 along an axis normal to the array 10 (indicated by arrow V) and in a plane parallel to the surface of the PEI layer 30 (indicated by arrow P). The actuator 60 accordingly controls the spring probe 50 to dip the delivery tip 70 into a well 80 containing a biomolecular fluid 90, position the spring probe 50 over a desired point of the PEI layer 30, and press the tip 70 against the desired point of the PEI layer 30. In another embodiment, the actuator 60 may only move the spring probe 50 normal to the array 10, and another actuator (not shown) translates the array 10 and the well 80 to position the tip 70 over the well 80 or a desired point of the PEI layer 30. The actuator 60 is preferably a robot or other computer controlled handling device that robotically delivers the biomolecular solution to the PEI layer 30. Additionally, a plurality of spring probes 50 may be attached to a single actuator to simultaneously deliver a plurality of biomolecule masses to the PEI layer 30.

Figure 2B:
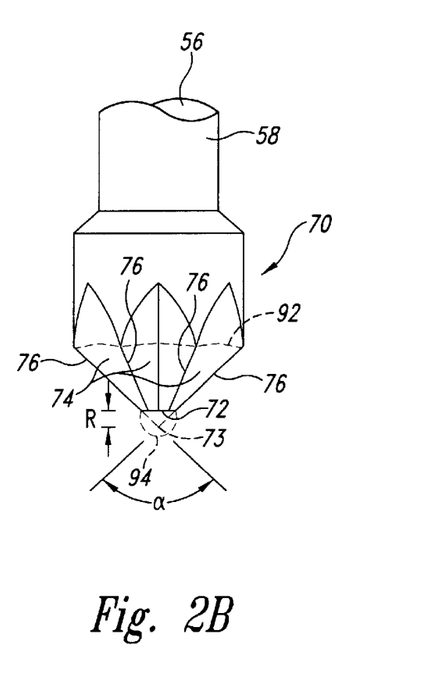
FIG. 2B is an enlarged front elevational view of an embodiment of a delivery tip in accordance with the invention.

The delivery tip 70 preferably draws a sufficient volume of biomolecular fluid 90 onto its surface to deliver a plurality of biomolecular masses onto the PEI layer 30 and form a corresponding plurality of implant regions 32 (shown in FIG. 1A) with a single pick-up step. FIG. 2B is an enlarged front elevational view of a delivery tip 70 in accordance with one embodiment of the invention. The delivery tip 70 preferably has a truncated-conical shape with a distal face 72 and a plurality of flutes or channels 74. The distal face 72 may be a flat surface recessed from an imaginary intersecting point 73 by a distance "R" between approximately 0.00001 in and 0.010 in, and more preferably between approximately between 0.001 in and 0.005 in. Additionally, the flutes 74 have vanes or ridges 76 converging toward the distal face 72 at an angle α between approximately 15° and 120°, and more preferably between 60° and 90°.

Figure 1B:
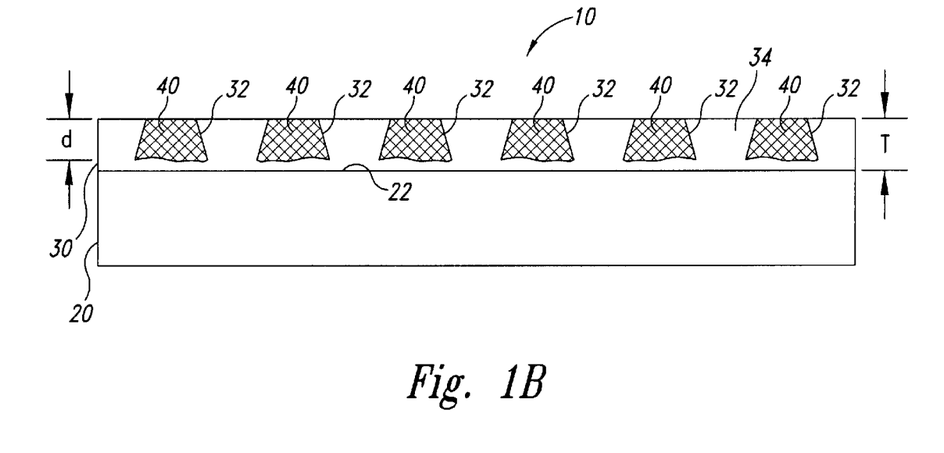
FIG. 1B is a schematic cross-sectional view of the array of FIG. 1A.

The spring probe 50, actuator 60 and delivery tip 70 operate together to deliver a controlled amount of biomolecular fluid to the PEI layer 30 each time the actuator 60 presses the delivery tip 70 against the PEI layer 30. The actuator 60 initially dips the delivery tip 70 into the well 80 of biomolecular fluid 90 to draw and hold a significant volume of biomolecular fluid 92 (FIG. 2B) onto the delivery tip 70 via capillary action. The actuator 60 then positions the spring probe 50 over the PEI layer 30. After removing the tip 70 from the well 80, a portion of the biomolecular fluid 92 on the tip 70 forms a hanging mass 94 of fluid at the distal face 72 of the tip. The actuator then presses the tip 70 against the PEI layer to form a single, discrete implant region 32 (shown in FIGS. 1A and 1B) of the array 10 from a portion of the biomolecular fluid on the tip 70. The actuator 60 preferably presses the tip 70 against the PEI layer 30 so that the tip 70 contacts the PEI layer 30 with a nominal amount of pressure. However, it is difficult consistently press the tip 70 against the PEI layer 70 with the same pressure because the actuator 60 may not always position the tip 70 at the same elevation and the surface of the PEI layer 70 may not be uniformly planar. The biasing member 54 accordingly stores energy caused by pressing the tip 70 against the PEI layer 30 permitting the spring probe 50 to contact the PEI layer 30 with a substantially constant pressure for each delivery irrespective of minor irregularities in the stroke of the actuator 60 or the topography of the PEI layer 30.

The delivery system described above accordingly provides an apparatus that can deliver a consistent implant volume of biomolecular fluid each time the tip 70 engages the PEI layer 30. It will be appreciated that a precise, consistent volume of biomolecular fluid should be delivered to the PEI layer 30 at each implant region 32 to maintain the spacer region 34 in the PEI layer 30. The quantity of the implanted biomolecular fluid 40 in the PEI layer 30 at an implant region 32 is generally determined empirically, and it is a function the time that the tip 70 engages the PEI layer 30, the viscosity of the biomolecular fluid 90, the configuration of the tip 70, and the pressure between the tip 70 and the PEI layer 30. Because the biasing member 54 provides a substantially constant pressure between the tip 70 and the PEI layer 30, the primary factor influencing the quantity of biomolecular fluid delivered to the PEI layer 30 is the time that the tip 70 engages the PEI layer 30.

Figure 3:
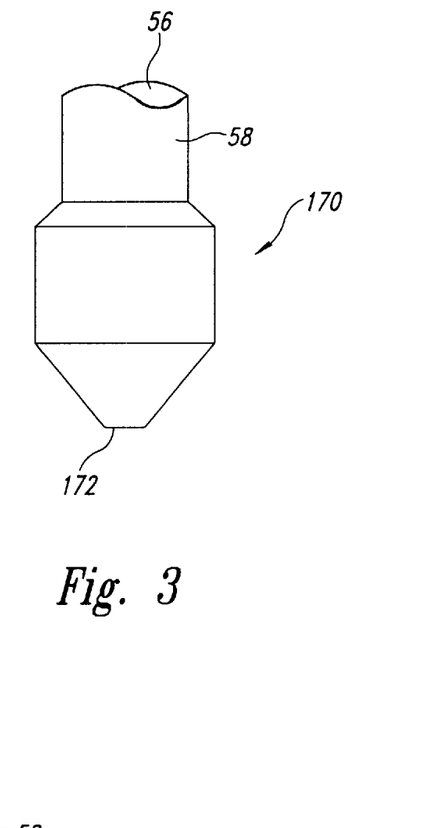
FIG. 3 is a front elevational view of another delivery tip with a conical design.

FIG. 3 is a front elevational view of another embodiment of a delivery tip 170 in accordance with the invention. In this embodiment, the delivery tip 170 has a truncated-conical shape with a distal face 172, but without flutes or vanes.

Accordingly, the delivery tip 170 holds the biomolecular fluid on the surface of the conical section of the tip. Although the delivery tip 170 may be used to deliver biomolecular fluid to the PEI layer 30, it is generally more desirable to use a fluted tip because such tip hold more biomolecular fluid.

Figure 4A:
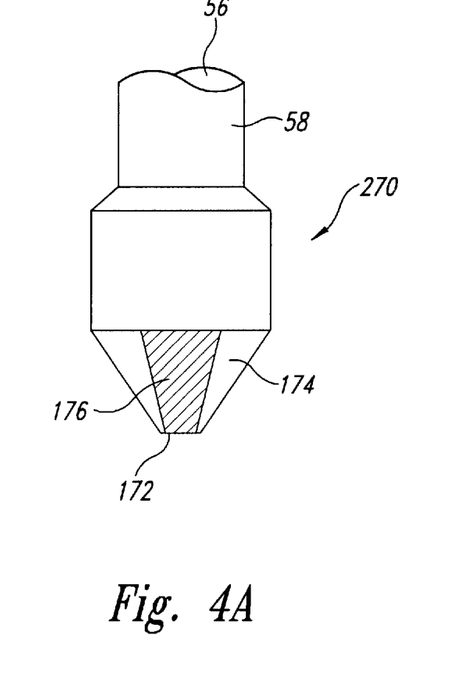
FIG. 4A is a front elevational view of yet another embodiment of a delivery tip with a fluted, conical design in accordance with another embodiment of the invention.
Figure 4B:
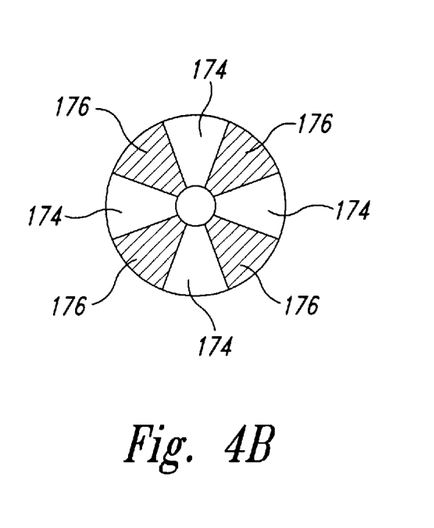
FIG. 4B is a bottom plan view of the delivery tip of FIG. 4A.

FIG. 4A is a front elevational view and FIG. 4B is a bottom plan view of yet another embodiment of a delivery tip 270 with a plurality of flutes 174 and vanes 176. The delivery tip 270 operates in substantially the same manner as the tip 70 described above, and thus it also provides substantially the same advantages.

The delivery tips 70, 170 and 270 described above represent a few examples of delivery tips that may be used to implant biomolecular fluid into the PEI layer 30. It will be appreciated that several modifications of the tips may be made, including using different shapes a distal face designs. For example, the tips may have pyramidal, cylindrical, cubical or other suitable shapes depending upon the particular application. Additionally, the flutes may have configurations other than those shown in the present figures. Thus, the delivery tips are not necessarily limited to those illustrated in FIGS. 2B–4B.

Biomolecule Solutions

The invention provides for compositions which may be used to deposit biomolecule onto a planar surface. The compositions are particularly well-suited for being transferred to a planar surface with the modified spring probes described above. When the compositions of the invention and are used in conjunction with the modified spring probes of the invention, multiple microdroplets (e.g., over 10 and preferably over 100) may be reproducibly deposited onto a planar surface after only a single liquid pickup.

The invention provides for a composition, also called an "arraying solution" containing a thickening agent at a concentration of about 35 vol % to about 80 vol % based on the total volume of the composition, a biomolecule which is preferably an oligonucleotide at a concentration ranging from 0.001 $\mu$g/mL to 10 $\mu$g/mL, and water. It has been surprisingly discovered that when a thickening agent is contained within an aqueous oligonucleotide composition, the thickening agent imparts desirable rheological properties to the composition, thus enabling the composition to be used with the modified spring probes disclosed herein, to deliver multiple uniform microdroplets to a planar surface having a PEI coating, with only a single pickup of the composition from the reservoir of composition.

The concentration of the thickening agent is 35% V/V to 80% V/V for liquid thickening agents such as glycerol. The preferred concentration of thickening agent in the composition depends, to some extent, on the temperature at which the arraying is performed. The lower the arraying temperature, the lower the concentration of thickening agent that needs to be used. The combination of temperature and viscosity control permits arrays to be made on most types of solid supports (e.g., glass, wafers, nylon 6/6, nylon membranes, etc.).

The presence of a thickening agent has the additional benefit of allowing the concurrent presence of low concentrations of various other materials to be present in combination with the biomolecule. For example 0.001% V/V to 1% V/V of detergents may be present in the arraying solution. This is useful because PCR buffer contains a small amount of TWEEN® 20 (polyoxyethylenesorbitan monolaurate) or NONIDET® P-40 (octylphenol ethoxylate), and it is frequently desirable to array sample nucleic acids directly from a PCR vial without prior purification of the amplicons. The use of a thickening agent permits the presence of salts (for example NaCl, KCl, or $MgCl_2$), buffers (for example Tris), and/or chelating reagents (for example EDTA) to also be present in the arraying solution. The use of a thickening agent also has the additional benefit of permitting the use of cross-linking reagents and/or organic solvents to be present in the arraying solution. As commercially obtained, cross-linking reagents are commonly dissolved in organic solvent such as DMSO, DMF, NMP, methanol, ethanol and the like. Commonly used organic solvents can be used in arraying solutions of the invention at levels of 0.05% to 20% (V/V) when thickening agents are used.

In general, the thickening agents impart increased viscosity to the arraying solution. When a proper viscosity is achieved in the arraying solution, the first drop is the substantially the same size as, for example, the 100th drop deposited. When an improper viscosity is used in the arraying solution, the first drops deposited are significantly larger than latter drops which are deposited. The desired viscosity is between those of pure water and pure glycerin.

The arraying solutions of the present invention may be used to deposit microdroplets onto almost any surface. Since, the surface property of the solid support has little or no effect on the deposition of the microdroplet, biological samples can be arrayed onto almost any type of coated surface or polymer-coated solid support. For example, typical aqueous solutions tend to spread rapidly on solid supports which are coated with hydrophilic polymers such as poly(lysine) or poly(ethylenimine) whereas these same solutions tend not to be easily deposited on hydrophobic surfaces such as silicon wafers. However, arraying solutions with a thickening agent according to the present invention may be used to deposit uniform microdots on any of these substrates.

Another important benefit of including a thickening agent such as glycerol in the arraying process is quality control. When glycerol, for example, is used in the arraying method as described herein, a small droplet of liquid is deposited on the solid support. At the concentrations commonly used in the methods described here, the glycerol concentration is sufficient to prevent evaporation of the microdroplet. Therefore, each printing of each array pin can be examined prior to chemical processing of the array. The ability to visualize microdroplets substantially enhances the ability to perform quality control with respect to the arraying process. This leads to a substantial increase in value in the arraying methodology.

The biomolecule may be a nucleic acid polymer or analog thereof, such as PNA, phosphorothioates and methylphosphonates. Nucleic acid refers to both ribonucleic acid and deoxyribonucleic acid. The biomolecule may comprise unnatural and/or synthetic bases. The biomolecule may be single or double stranded nucleic acid polymer.

A preferred biomolecule is an nucleic acid polymer, which includes oligonucleotides (up to about 100 nucleotide bases) and polynucleotides (over about 100 bases). A preferred nucleic acid polymer is formed from 15 to 50 nucleotide bases. Another preferred nucleic acid polymer has 50 to 1,000 nucleotide bases. The nucleic acid polymer may be a PCR product, PCR primer, or nucleic acid duplex, to list a few examples. However, essentially any nucleic acid type can be covalently attached to a PEI-coated surface when the nucleic acid contains a primary amine, as disclosed below. The typical concentration of nucleic acid polymer in the arraying solution is 0.001–10 µg/mL, preferably 0.01–1 µg/mL, and more preferably 0.05–0.5 µg/mL.

Preferred nucleic acid polymers are "amine-modified" in that they have been modified to contain a primary amine at the 5'-end of the nucleic acid polymer, preferably with one or more methylene (—$CH_2$—) groups disposed between the primary amine and the nucleic acid portion of the nucleic acid polymer. Six is a preferred number of methylene groups. Amine-modified nucleic acid polymers are preferred because they can be covalently coupled to a solid support through the 5'-amine group. PCR products can be arrayed using 5'-hexylamine modified PCR primers. Nucleic acid duplexes can be arrayed after the introduction of amines by nick translation using amine allyl-dUTP (Sigma, St. Louis, Mo.). Amines can be introduced into nucleic acids by polymerases such as terminal transferase with amino allyl-dUTP or by ligation of short amine-containing nucleic acid polymers onto nucleic acids by ligases.

Preferably, the nucleic acid polymer is activated prior to be contacted with the PEI coating. This can be conveniently accomplished by combining amine-functionalized nucleic acid polymer with a multi-functional amine-reactive chemical such as trichlorotriazine. When the nucleic acid polymer contains a 5'-amine group, that 5'-amine can be reacted with trichlorotriazine, also known as cyanuric chloride (Van Ness et al., *Nucleic Acids Res.* 19(2):3345–3350, 1991) Preferably, an excess of cyanuric chloride is added to the nucleic acid polymer solution, where a 10- to 1000-fold molar excess of cyanuric chloride over the number of amines in the nucleic acid polymer in the arraying solution is preferred. In this way, the majority of amine-terminated nucleic acid polymers have reacted with one molecule of trichlorotriazine, so that the nucleic acid polymer becomes terminated with dichlorotriazine.

An advantageous feature of the present invention is that the biomolecule-containing arraying solutions may be deposited onto a PEI coating even though that arraying solution contains a significant amount of trichlorotriazine. This provides a significant advantage over methods wherein coupling agent needs to be removed from an arraying solution prior to an arraying process.

When the nucleic acid polymer is double stranded, a preferred embodiment of the invention provides that both strands or one of the strands contains a terminal amino group. The double stranded nucleic acid polymer may be bonded through one terminal amino group to the PEI coating, to thereby immobilize the double stranded polymer. However, since only one of the two strands is covalently bonded to the PEI coating, the other strand may be removed under denaturing and washing conditions. This approach provides one convenient method according to the present invention of achieving an array of single stranded nucleic acid polymers. The double stranded nucleic acid polymer may be obtained, for example, as a reaction product from PCR.

Preferably, the arraying solution is buffered using a common buffer such as sodium phosphate, sodium borate, sodium carbonate, or Tris HCl. A preferred pH range for the arraying solution is 7 to 9, with a preferred buffer being freshly prepared sodium borate at pH 8.3 to pH 8.5.

To prepare a typical arraying solution, hexylamine-modified nucleic acid polymer is placed in 0.2 M sodium borate, pH 8.3, at 0.1 µg/mL, to a total volume of 50 µl. Ten µl of a 15 mg/mL solution of cyanuric chloride is then added, and the reaction is allowed to proceed for 1 hour at 25 C with constant agitation. Glycerol (Gibco Brl®, Grand Island, N.Y.) is added to a final concentration of 56%.

Solid Supports

The invention provides a method for depositing biomolecule onto a solid support, which includes the steps of: immersing a tip of a spring probe into a solution of biomolecule; removing said tip from said solution to provide biomolecule solution adhered to said tip; and contacting said biomolecule solution with a solid support to thereby transfer biomolecule solution from said tip to said solid support. The solid support preferably has a planar surface upon which the biomolecule is deposited.

An example of a solid support that is useful for this purpose is a silicon wafer that is typically used in the electronics industry in the construction of semiconductors. The wafers are highly polished and reflective on one side and can be easily coated with poly(ethylenimine) using silane chemistries. The wafers are commercially available from companies such as WaferNet, (San Jose, Calif.). The coating of wafers and glass slides with polymers such as poly(ethylenimine) can be performed under contract through companies such as Cel Associates (Houston, Tex.). Glass slides can also be coated with a reflective coating. Glass slides with a reflective coating can also be easily coated with poly(ethylenimine) using silane chemistries.

The polymer coating of poly(ethylenimine) permits the covalent attachment of oligonucleotides, PCR fragments or amplicons, DNA molecules or fragments or other amine-containing biomolecules to the solid support using commercially available cross-linkers (Pierce, Rockford, Ill.). Poly (ethylenimine) (PEI) coated slides also have the added benefit of long shelf life stability.

Another desirable solid support is a metal, e.g., stainless steel. Such metal solid supports may be used as substrate in MALDI-TOF analysis, where the elements being analyzed by MALDI-TOF were deposited using the printing process as disclosed herein.

Arraying Conditions and Post-Arraying Treatments

The arraying solutions as described above may be used directly in an arraying process. That is, in a preferred embodiment for arraying nucleic acid polymers, the activated nucleic acid polymers are not purified away from unreacted cyanuric chloride prior to the printing step. It has been surprisingly discovered that there is no need to remove the excess crosslinker prior to printing in the arraying method. That is, the excess cyanuric chloride in the reaction mixture does not interfere or compete with the covalent attachment of the nucleic acid polymers to a PEI coated solid support. This is because there is an excess of amines on the solid support over the number of cyanuric chloride molecules that will be arrayed at any given volume (nanoliters to picoliters).

Typically the reaction which attaches the activated nucleic acid to the solid support is allowed to proceed for 1 to 20 hours at 20 to 50 C. Preferably, the reaction time is 1 hour at 25 C.

The arrays of the present invention are particularly useful in conducting hybridization assays. However, in order to perform such assays, the amines on the solid support must be capped prior to conducting the hybridization step. This may be accomplished by reacting the solid support with 0.1–2.0 M succinic anhydride. The preferred reaction conditions are 1.0 M succinic anhydride in 70% m-pyrol and 0.1 M sodium borate. The reaction typically is allowed to occur for 15 minutes to 4 hours with a preferred reaction time of 30 minutes at 25 C. Residual succinic anhydride is removed with a 3×water wash.

The solid support is then incubated with a solution containing 0.1–5 M glycine in 0.1–10.0 M sodium borate at pH 7–9. This step "caps" any dichloro-triazine which may be covalently bound to the PEI surface. The preferred conditions are 0.2 M glycine in 0.1 M sodium borate at pH 8.3.

The solid support may then be washed with detergent-containing solutions to remove unbound materials, for example, trace m-cyrol.

Preferably, the solid support is heated to 95C. in 0.01 M NaCl, 0.05 M EDTA and 01 M Tris pH 8.0 for 5 minutes. This heating step removes non-covalently attached nucleic acid polymers, such as PCR products. In the case where double strand nucleic acid are arrayed, this step also has the effect of converting the double strand to single strand form (denaturation).

The arrays are may be interrogated by probes (e.g., oligonucleotides, nucleic acid fragments, PCR products, etc.) which are biotinylated. The methods for biotinylating nucleic acids are well known in the art and are adequately described by Pierce (Avidin-Biotin Chemistry: A Handbook, Pierce Chemical Company, 1992, Rockford Ill.). Probes are generally used at 0.1 ng/mL to 10/μg/mL in standard hybridization solutions that include GuSCN, GuHCl, formamide, etc. (see Van Ness and Chen, *Nucleic Acids Res.*, 19:5143–5151, 1991).

To detect the hybridization event (i.e., the presence of the biotin), the solid support is incubated with streptavidin/horseradish peroxidase conjugate. Such enzyme conjugates are commercially available from, for example, Vector Laboratories (Burlingham, Calif.). The streptavidin binds with high affinity to the biotin molecule bringing the horseradish peroxidase into proximity to the hybridized probe. Unbound streptavidin/horseradish peroxidase conjugate is washed away in a simple washing step. The presence of horseradish peroxidase enzyme is then detected using a precipitating substrate in the presence of peroxide and the appropriate buffers.

A blue enzyme product deposited on a reflective surface such as a wafer has a many-fold lower level of detection (LLD) compared to that expected for a calorimetric substrate. Furthermore, the LLD is vastly different for different colored enzyme products. As shown in Example 5, the LLD for 4-methoxy-napthol (which produces a precipitated blue product) per 50 μM diameter spot is approximately 1000 molecules, whereas a red precipitated substrate gives an LLD about 1000-fold higher at 1,000,000 molecules per 50 μM diameter spot. The LLD is determined by interrogating the surface with a microscope (such as the Axiotech microscope commercially available from Zeiss) equipped with a visible light source and a CCD camera (Princeton Instruments, Princeton, N.J.). An image of approximately 10,000 μM×10,000 μM can be scanned at one time.

In order to use the blue calorimetric detection scheme, the surface must be very clean after the enzymatic reaction and the wafer or slide must be scanned in a dry state. In addition, the enzymatic reaction must be stopped prior to saturation of the reference spots. For horseradish peroxidase this is approximately 2–5 minutes.

It is also possible to use chemiluminescent substrates for alkaline phosphatase or horseradish peroxidase (HRP), or fluorescence substrates for HRP or alkaline phosphatase. Examples include the diox substrates for alkaline phosphatase available from Perkin Elmer or Attophos HRP substrate from JBL Scientific (San Luis Obispo, Calif.).

Robotic Delivery of Biomolecule Solution

The invention provides a method for depositing a biomolecule onto a solid support, which includes the steps of: immersing a tip of a spring probe into a solution of biomolecule; removing the tip from the solution to provide biomolecule solution adhered to the tip; and contacting the biomolecule solution with a solid support to thereby transfer biomolecule solution from the tip to the solid support. In a preferred embodiment, the contacting step is accomplished robotically. In other words, a precision robotic system which can be controlled in the x, y and z axis. A precision Cartesian robotic system would consist of linear positioning tables coupled with the appropriate motors, amplifiers, motion controller, personal computer and software to drive the tables. Precision linear positioning tables are available from Parker Hannifin Corporation (Daedel Division, Harrison City, Pa.) or THK Company, Ltd. (Tokyo, Japan). Motors, amplifiers, and motion controllers are available from Parker Hannifin Corporation (Daedel Division, Harrison City, Pa.) or Galil Motion Control, Inc. (Mountain View, Calif.). Software would mostly likely be custom and could be written in a language such as Borland C++ 4.5 (Borland International Inc., Scotts Valley, Calif.) or Visual Basic 4.0 (Microsoft Corporation, Redmond, Wash.). Personnel computers are available from numerous manufacturers such as Dell Computer Corporation (Austin, Tex.).

Spring probes as described above are manufactured to be mounted into any of several styles of receptacle, and robots useful in the present invention contain suitably sized receptacles to accept the spring probe. Preferred receptacles are made from nickel-silver or bronze, then gold plated over hard nickel. A design for a preferred receptacle is a metal tube with diameter 1.5 mm to 2.0 mm, more preferably 1.68 millimeters. A square wire 0.5 mm to 1 mm thick, more preferably 0.64 mm thick is crimped into one end of the tube and sealed. Each receptacle is manufactured with an indent and press ring to hold a spring probe securely. The probe is inserted into the receptacle so the barrel of the probe is flush with the receptacle end.

A mounting head is mounted onto a robot for the purpose of arraying liquid. The head has a bar which is interchangeable for various printing applications. Bars can be easily changed by removing two screws, and replacing one bar designed for arraying from a 96 well plate with one designed to hold spring probes designed to array from a 384 well plate, for example. The receptacles are held in the bar by friction using precision-drilled, bi-level holes to fit the wire wrap and crimped region of the receptacle snugly. This design allows easy replacement of damaged or poorly performing receptacle and/or spring probes. Once inserted, the receptacle/spring probe unit extends down from the bar a distance of 25 mm, thus allowing the probe to reach the bottom of the microtiter plate holding a sample liquid to be arrayed.

The printing processes and solutions, and methods of depositing biomolecule as described herein may be used to prepare arrays. Those arrays may be used in various assays, where those assays may include tagged biomolecules as probes (e.g., tagged oligonucleotides). Exemplary tagged biomolecules, and assays which may use the same, are described in U.S. patent application Ser. Nos. 08/786,835; 08/786,834 and 08/787,521, each filed on Jan. 22, 1997 (now abandoned), as well as in three U.S. continuation-in-part patent applications having application Ser. Nos. 08/898,180; 08/898,564 (now pending); and 08/898,501 (now issued as U.S. Pat. No. 6,027,890), each filed July 22, 1997, and PCT International Publication Nos. 97/27331; 97/27325; and 97/27327. These six U.S. Patent applications and three PCT International Publications are each hereby fully incorporated herein by reference in their entireties.

In addition, the apparatus and methods of the present invention may be used to prepare arrays containing more than one oligonucleotide sequence within an element. Biomolecule arrays containing more than one oligonucleotide sequence within an element, and uses thereof, are described in our U.S. patent application Ser. No. 09/120,688 titled "Multiple Functionalities Within An Array Element And Uses Thereof" filed concurrently herewith (now pending), which claims the priority benefit of U.S. Provisional Patent Application No. 60/053,436 filed Jul. 22, 1997, both of which are hereby fully incorporated herein by reference in their entireties.

The apparatus and methods of the present invention may also be used to prepare arrays useful in performing amplification and other enzymatic reactions, as described in our U.S. patent application Ser. No. 09/120,501 titled "Amplification And Other Enzymatic Reactions Performed On Nucleic Acid Arrays" filed concurrently herewith (now allowed), which claims the priority benefit of U.S. Provisional Patent Application No. 60/053,428 filed Jul. 22, 1997, both of which are hereby fully incorporated herein by reference in their entireties.

The apparatus and methods of the present invention may be employed to prepare biomolecule arrays as disclosed in our U.S. patent application Ser. No. 09/120,386 titled "Polyethylenimine-Based Biomolecule Arrays" filed concurrently herewith (now issued as U.S. Pat. No. 6,150,103), which claims the priority benefit of U.S. Provisional Patent Application No. 60/053,352 filed Jul. 22, 1997, both being fully incorporated herein by reference in their entireties.

Computer systems and methods for correlating data, as disclosed in U.S. patent application Ser. No. 09/120,686 titled "Computer Method and System For Correlating Data" filed concurrently herewith (now pending), which claims the priority benefit of U.S. Provisional Patent Application No. 60/053,429 filed Jul. 22, 1997 (both being fully incorporated herein by reference in their entireties) may be used in combination with the methods and apparatus as described herein.

The invention has great utility for a number of biotechnological applications, specifically those methods relating to developing large scale diagnostic screening methods utilizing the polymerase chain reaction (PCR), nucleic acid hybridization, nucleic acid sequencing by hybridization, replicating of viral, bacterial or cellular libraries, as well as any other methods that involve the repetitive arraying of solutions onto solid surfaces.

The following examples are offered by way of illustration, not limitation.

EXAMPLES

Example 1

One Step Process for Preparation of PEI-Coated Glass Slide

A glass slide is washed with 0.1 N acetic acid, then rinsed with water until the water rinsed from the slide has a pH equal to the pH of the water being used to rinse the slide. The slide is then allowed to dry.

To a 95:5 ethanol:water solution is added a sufficient quantity of a 50% w/w solution of trimethoxysilylpropyl-polyethylenimine (600 MW) in 2-propanol (Gelest, Inc., Tullytown, Pa., Catalog No. SSP060) to achieve a 2% w/w final concentration. After stirring this 2% solution for five minutes, the glass slide is dipped into the solution, gently agitated for 2 minutes, and then removed. The glass slide is dipped into ethanol in order wash away excess silylating agent. The glass slide is then air dried.

Example 2

One-Step Process for Preparation of PEI-Coated Silicon Wafer

A silicon wafer (WaferNet, San Jose, Calif.) is washed with 0.1 N acetic acid, then rinsed with water until the water rinsed from the wafer has a pH equal to the pH of the water being used to rinse the wafer. The wafer is then allowed to dry.

To a 95:5 ethanol:water solution is added a sufficient quantity of a 50% w/w solution of trimethoxysilylpropyl-polyethylenimine (600 MW) in 2-propanol (Gelest, Inc., Tullytown, Pa., Catalog No. SSP060) to achieve a 2% w/w final concentration. After stirring this 2% solution for five minutes, the silicon wafer is dipped into the solution, gently agitated for 2 minutes, and then removed. The wafer is dipped into ethanol in order wash away excess silylating agent. The silicon wafer is then air dried.

Example 3

Two-Step Process for Preparation of PEI-Coated Glass Slide

A glass slide is washed with 0.1 N acetic acid, then rinsed with water until the water rinsed from the slide has a pH equal to the pH of the water being used to rinse the slide. The slide is then allowed to dry.

To a 95:5 ethanol:water solution is added a sufficient quantity of an electrophilic silylating agent, with stirring to achieve a 2% w/w final concentration. The electrophilic silylating agent is one of 2-(3,4-epoxycyclohexyl) ethyltrimethoxysilane (Gelest, Inc., Catalog No. SIE4670.0), 3,4-epoxybutyltrimethoxysilane (Gelest, Inc., Catalog No. SIE4665.0) or 3-isocyanatopropyltriethoxysilane (Gelest, Inc., Catalog No. SII6454.0). After stirring this 2% solution for five minutes, the glass slide is dipped into the solution, gently agitated for 2 minutes, and then removed. The glass slide is dipped into ethanol in order wash away excess silylating agent.

A 3% (w/v) solution of 70,000 molecular weight poly (ethylenimine) is prepared by diluting a 30% aqueous solution of poly(ethylenimine) (Polysciences, Warrington, Pa.) with 1-methyl-2-pyrrolidone (NMP). The treated glass slide is dipped into the 3% solution and gently agitated for 24 hours. In order to remove excess PEI from the slide, the glass slide is dipped into NMP (2×), followed by dipping into a 0.1% aqueous solution of sodium dodecyl sulfate also containing 0.09 M NaCl, 50 mM Tris pH 7.6 and 25 mM EDTA (2×), then dipping into water (2×), and finally dipping into ethanol (1×). The glass slide is then allowed to air dry.

Example 4

Two-Step Process for Preparation of PEI-Coated Silicon Wafer

A silicon wafer (WaferNet, San Jose, Calif.) is washed with 0.1 N acetic acid as described in Example 3, following by treatment with a silylating agent and PEI, also as described in Example 3.

Example 5

Praparation of Arraying Tip from a Commercial Spring Probe

XP54P spring probes were purchased from Osby-Barton (a division of Everett Charles (Pomona, Calif.)). A probe was directed "tip-down" against an extra fine diamond sharpening stone (DMT Inc., Miami Lattes, Fla.) and moved across the stone for a distance of about 0.5 cm with gentle pressure. Approximately 0.005 inches (0.001 to 0.01 inches) of metal was thereby removed from the end of the tip as observed by microscopy. The tip end was then polished by rubbing the tip across a leather strip. The tip was then washed with water. Before initial use, or between uses, the tip was stored dry or in 50% glycerol at −20° C.

Example 6

Assembly of Arraying Device with Modified Spring Probe

The tip as prepared in Example 5 was mounted into an arraying head mounted on a precision robotic system which can be controlled in the x, y and z axis. The precision Cartesian robotic system consists a of linear positioning table coupled with the appropriate motors, amplifiers, motion controller, personal computer and software to drive the tables. Precision linear positioning tables are available from Parker Hannifin Corporation (Daedel Division, Harrison City, Pa.) or THK Company, Ltd. (Tokyo, Japan). Motors, amplifiers, and motion controllers are available from Parker Hannifin Corporation (Daedel Division, Harrison City, Pa.) or Galil Motion Control, Inc. (Mountain View, Calif.).

Example 7

The use of a Hydrophilic Surface to Promote Liquid Pickup, Liquid Transfer and Micro-Droplet Deposition The tip of a spring probe according to Example 5 is soaked in a solution of 100 mM 1,4-dithiothreitol and 0.1 M sodium borate for 60 minutes. Dithiothreitol will react with a gold surface through thiol-gold coordination to make the surface of the gold hydrophilic (the surface is essentially hydroxylated).

Example 8

Preparation of Reactive Oligonucleotide

75 µl of a solution of 5'-hexylamine-GTCATACTCCTGCTTGCTGATCCACATCTG-'3 (SEQ ID NO:1) (0.5 µg/µl) was reacted with 5 µl of 20 mg/ml cyanuric chloride and 20 µl of 1M sodium borate for 30 minutes at room temperature.

Example 9

Arraying Solution of Oligonucleotide

An arraying solution was prepared which consists of 12.5 µL 1 M sodium borate pH 8.3 (freshly prepared or thawed from a stock at −20° C.), 50 µl 0.1 µg/µL 5' hexylamine oligonucleotide (5' hexylamine-GTCATACTCCTGCTTGCTGATCCACATCTG-3'; SEQ ID NO:1), 7.5 µL of 15 mg/mL cyanuric chloride in acetonitrile. This mixture was allowed to incubate at room temperature for 30 to 60 minutes. 155 µL of 80% glycerol was then added to the solution and the resulting solution was mixed well. In some cases, 15 µL of 10% NONIDET® P-40 (octylphenol ethoxylate) or 10% TWEEN® 20 (polyoxyethylenesorbitan monolaurate) or 10% TRITON® X-100 (polyoxyethylene(10) isooctylphenyl ether) (Rohm and Haas, Philadelphia, Pa.) is added to the solution. When the arraying substrate is composed of nylon or nitrocellulose membranes, 25 µL of 5 M NaCl is added to the arraying solution.

Example 10

Arraying Solution of PCR Amplicons

When PCR amplicons are to be arrayed, 2.5 µL 1 M sodium borate pH 8.3 (freshly prepared or thawed from a stock at −20° C.), 50 µl 0.1 µg/µL 5' hexylamine oligonucleotide (5' hexylamine-GTCATACTCCTGCTTGCTGATCCACATCTG-3'; SEQ ID NO: 1), 7.5 µL of 15 mg/mL cyanuric chloride in acetonitrile are added to the PCR tube containing the PCR contents after the thermocycling step is complete. This mixture is allowed to incubate at room temperature for 30 to 60 minutes. 155 µL of 80% glycerol is then added to the solution and the resulting solution is mixed well. In some cases 15 µL of 10% NONIDET® P-40 (octylphenol ethoxylate), or 10% TWEEN® 20 (polyoxyethylenesorbitan monolaurate) or 10% TRITON® X-100 (polyoxyethylene (10) isooctylphenyl ether) is added to the solution. When the arraying substrate is composed of nylon or nitrocellulose membranes, 25 µL of 5 M NaCl is added to the arraying solution.

Example 11

Preparation of Arrayed Oligonucleotides

The modified spring probe of Example 5 is positioned in a robotic delivery device according to Example 6, and the spring probe tip is conditioned according to Example 7. The tip is submerged 5 millimeters into the arraying solution of Example 9 for 2 seconds. The solution-bearing tip is then used by the robot to print 72 microspots in a 12×6 grid onto a polyethylenimine (PEI) coated silicon wafer prepared according to any of Examples 2, 4, or as provided by Cell Associates (Houston, Tex.) or the like, who will prepare PEI-coated substrates under contract. The spots produced were approximately 100–150 microns in diameter with 200 microns between the centers of neighboring spots.

Example 12

Blocking of Active PEI Sites

The array of Example 11 is treated with 100 mg/mL succinic anhydride in 100% NMP for 15 minutes, in order to block unreacted PEI sites on the array. This was followed by a water wash (3×).

Example 13

Blocking of Unreacted Cyanuric Chloride Sites

The array of Example 12 is treated with 0.1 M glycine in 0.01 M Tris for 15 minutes, followed by 4 washes with Tens (0.1 M NaCl, 0.1% SDS, 0.01 M Tris, 5 mM EDTA), in order to block unreacted cyanuric chloride sites on the array.

Example 14

Hybridization Process

The immobilized oligonucleotides in the array of Example 13 were hybridized to their biotinylated complement (5'-BIOTIN-CATACTCCTGCTTGCTGA TCCACA-3', SEQ ID NO:4; SEQ ID NO:2) for 20 minutes at 37° C.

with a 6×Tens, 2×OHS (0.06 M Tris, 2 mM EDTA), 5×Denhardt's solution, 6×SSC (3 M NaCl, 0.3 M sodium citrate, pH 7.0), 3.68 mM N-lauroylsarcosine, 0.005% NONIDET® P-40 (octylphenol ethoxylate)) wash.

Figure 5:
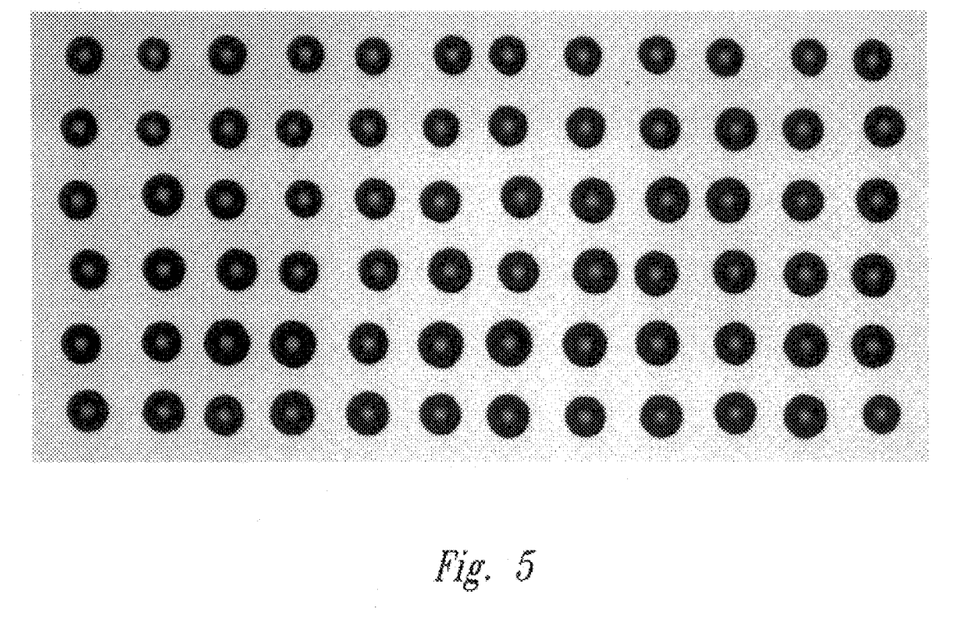
FIG. 5 shows an array of microspots prepared according to the invention and developed using Vector Blue (Vector Laboratories, Burlingame, Calif.) and imaged with a CCD camera and microscope.

Following hybridization, the wafer was soaked in 0.5 µg/ml alkaline phosphatase streptavidin for 15 minutes with a 2×Tens, 4×TWS (0.1 M NaCl, 0.1% TWEEN® 20 (polyoxyethylenesorbitan monolaurate), 0.05 M Tris) wash. The microspots were then developed using Vector Blue (Vector Laboratories, Burlingame, Calif.) (following kit protocol) and imaged with a CCD camera and microscope. FIG. 5 displays the image generated.

Example 15

Multiple Oligos within a Single Array Element

Two template oligos (oligo #1=5'-hexylamine-CATACTCCTGCTTGCTGA TCCACA-3', SEQ ID NO:4, oligo #2=5'-hexylamine-ACTACTGATCAGGCGCGCCTT TTTTTTTTTTTTTTTTT-3', SEQ ID NO:3) both concentrated at 0.5 µg/µl were reacted separately with 5 µl of 20 mg/ml cyanuric chloride an 20 µl of 1M sodium borate for 30 minutes at room temperature (total reaction volume=100 µl). From these two reactions, arraying solutions were made which consisted of 56% glycerol and diluted combinations of the two oligos (see Table 1). Eight arraying tips were submerged 5 millimeters into each of the eight arraying solutions for 2 seconds. The solution-bearing tips were then used by a robot to print two sets of eight 12×6 grids each containing 72 microspots onto a polyethylenimine (PEI) coated silicon wafer. Each grid represents a single arraying solution. The spots produced were approximately 100–150 microns in diameter with 200 micron center to center spacing between spots.

Following arraying, the unreacted PEI sites on the wafer were blocked with 100 mg/ml succinic anhydride in 100% N-methyl pyrrolinidone for 15 minutes with a 3×water wash. The unreacted cyanuric chloride sites were blocked with 0.1M glycine in 0.01 M Tris for 15 minutes with a 4×Tens (0.1 M NaCl, 0.1% SDS, 0.01 M Tris, 5 mM EDTA) wash. Two hybridizations were then carried out.

In the first hybridization, one set of the eight arrayed oligo combinations was hybridized to the biotinylated oligo (5'-BIOTIN-TGTGGATCAGCAAGCAGGAGTATG-3'; SEQ ID NO:2) complementary to oligo #1. In the second hybridization, the other set of the eight arrayed oligo combinations was hybridized to the biotinylated oligo (5'-BIOTIN-AAAAAAAAAAAAAAAAAAAAAGGCGCGCCTGATC AGTAGT; SEQ ID NO:3) complementary to oligo #2. The hybridizations were conducted simultaneously under Hybriwell Sealing Covers (Research Products International Corporation, Mount Prospect, Ill.) for 20 minutes at 37° C. with a 6×Tens, 2×OHS (0.06 M Tris, 2 mM EDTA), 5×Denhardt's solution, 6×SSC (3 M NaCl, 0.3 M sodium citrate, pH 7.0), 3.68 mM N-lauroylsarcosine, 0.005% NONIDET® P-40 (octylphenol ethoxylate)) wash.

Following hybridization, the wafer was soaked in 0.5 µg/ml horseradish peroxidase streptavidin for 15 minutes with a 2×Tens, 4×TWS (0.1 M NaCl, 0.1% TWEEN® 20 (polyoxyethylenesorbitan monolaurate), 0.05 M Tris) wash. The microspots were then developed using 0.4 mg/ml 4-methoxy-1-napthol (0.02% hydrogen peroxide, 12% methanol, PBS) with a final 3×water wash.

Figure 6:
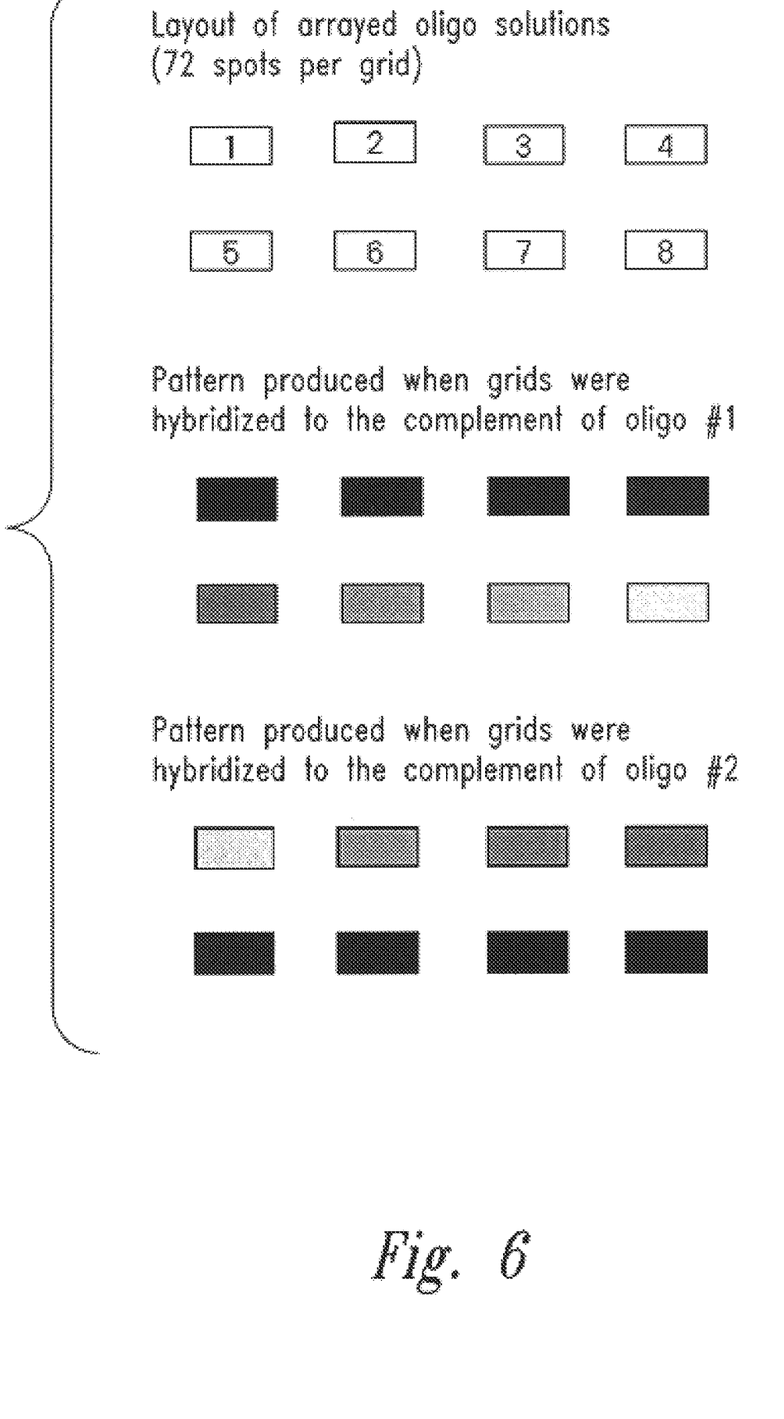
FIG. 6 is an illustration showing how two different oligonucleotides, both present within a single array element, may be identified and partially quantified according to the present invention.

The set of mixed oligos hybridized to the complement of oligo #1, showed the greatest color intensity for the grid containing the highest concentration of oligo #1 and the least color intensity with the grid containing the lowest concentration of oligo #1. However, the set of mixed oligos hybridized to the complement of oligo #2, showed the greatest color intensity for the grid containing the highest concentration of oligo #2 and the least color intensity with the grid containing the lowest concentration of oligo #2 (see FIG. 6).

TABLE 1

| Arraying Solution | Concentration of oligo in arraying solution (ng/µl) Oligo #1 | Concentration of oligo in arraying solution (ng/µl) Oligo #2 |
|---|---|---|
| 1 | 56 | 0.44 |
| 2 | 28 | 0.88 |
| 3 | 14 | 1.8 |
| 4 | 7 | 3.5 |
| 5 | 3.5 | 7 |
| 6 | 1.8 | 14 |
| 7 | 0.88 | 28 |
| 8 | 0.44 | 56 |

Example 16

Determining Element Size Consistency

Figure 7:
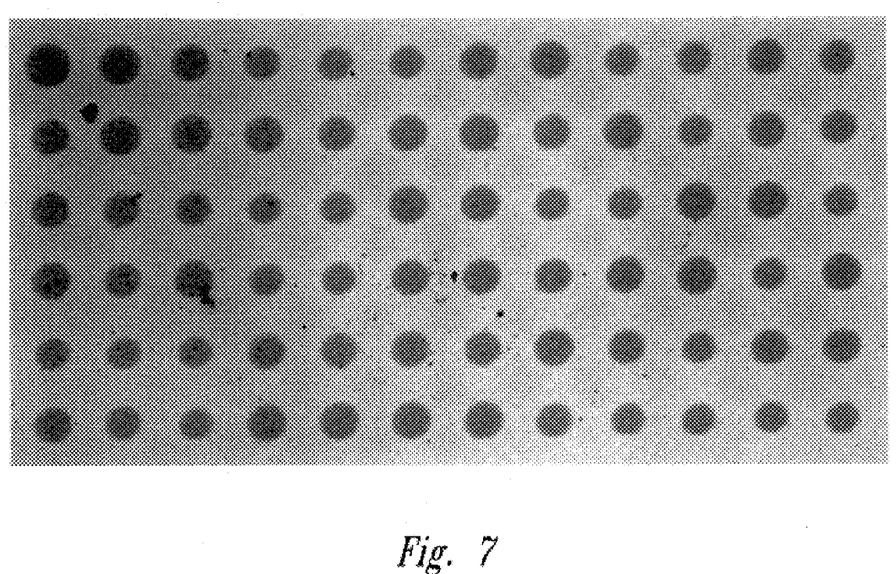
FIG. 7 shows a CCD camera image of an array produced by a robot using the methodology of the invention, where the domains are approximately 100–150 microns in average diameter with 200 micron center to center spacing between spots. The standard deviation of spot diameter is approximately 15%.

An arraying solution was made which consists of 56% glycerol and 44% water colored with blue food color. The arraying tip was submerged 5 millimeters into the arraying solution for 2 seconds. The glycerol bearing tip was then used by a robot to print 72 microspots in a 12×6 grid onto a silicon wafer. The spots produced were approximately 100–150 microns in diameter with 200 micron center to center spacing between spots. FIG. 7 shows a CCD camera image of the grid produced by the robot. The standard deviation of spot diameter is approximately 15%.

Example 17

Determining Reproducibility within Arraying Pocess

Figure 8:
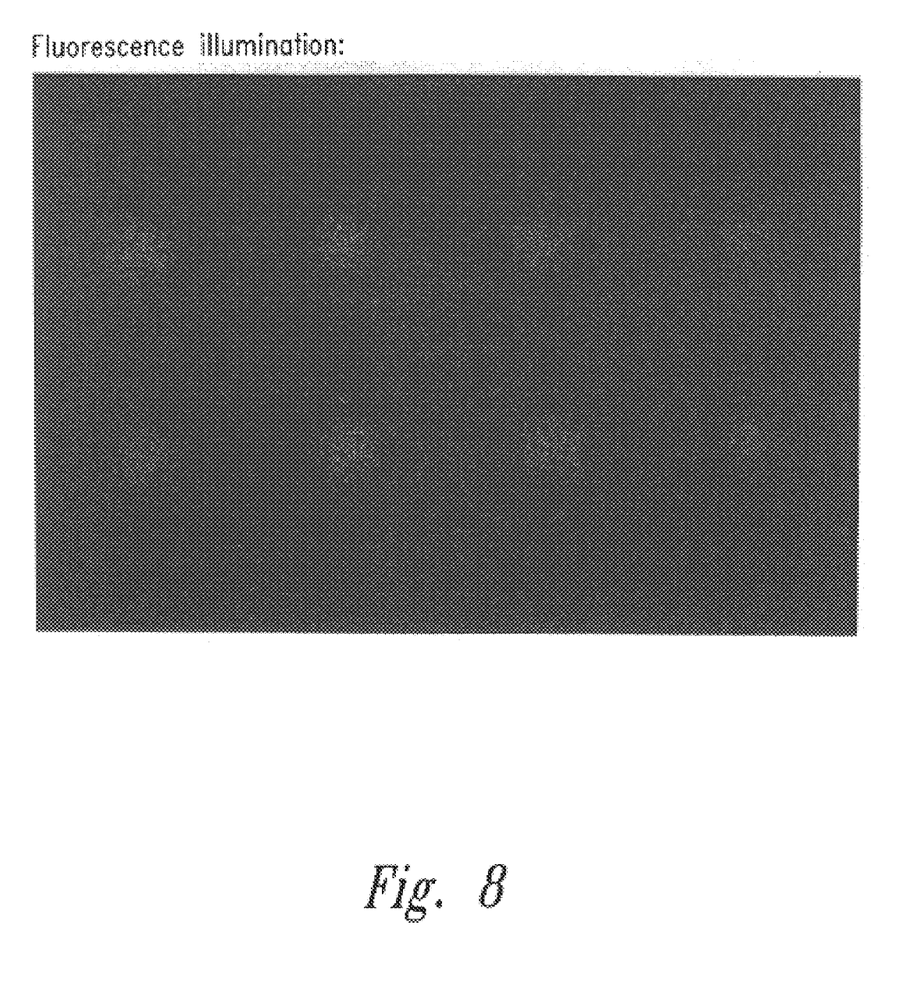
FIG. 8 is a photomicrographs made under fluorescence light using a filter for fluorescence, which demonstrates the reproducible deposition (as determined by visual inspection) of non-vehicle components (in this case, fluorescent microspheres) delivered from an assaying solution.

An arraying solution was made which consists of 56% glycerol, 0.01 M Tris pH 7.2, 5 mm EDTA, 0.01% Sarkosyl, and 1% V/V Fluoresbrite Plain 0.5 µM microspheres (2.5% Solids-latex), (Polysciences, Warrington, Pa.). The arraying pin was submerged 5 millimeters into the solution for 5 seconds and then used to print multiple microspots onto a glass slide. Photomicrographs were then made under fluorescence light using a filter for fluorescence. FIG. 8 demonstrates very reproducible deposition (as determined by visual inspection) of the fluoroescent microspheres with each of the microspots (array elements).

Example 18

Determining Nucleic Acid Polymer Concentration Per Element

Oligonucleotide (5'-Texas Red-CAGATGTGGATCAGCAAGCAGGAGTATGAC; SEQ ID NO:6) complementary to arrayed oligonucleotide was hybridized to the array in 3 M guanidinium thiocyanate (GuSCN), 0.01 M Tris, pH 7.5, 5 mM EDTA and 0.1% Sarkosyl. The volume was sufficient to cover the solid support (1 mL for a glass slide (1×3 inches)). The concentration of the Texas Red oligonucleotide was 5 µg/ml and the reaction was carried out at room temperature. The hybridization was allowed to proceed for 30 minutes. The slide was then washed with Tens (5×). The slide was then covered with 1 mL of elution buffer (0.005 M Tris pH 7.6, 0.0005 M EDTA, 0.01% Sarkosyl) and heated to 95° C. for 2 minutes. The solution was removed from the slide and placed into a black microtiter plate. Fluorescence was measured in a black microtiter plate. The solution was removed from the incubation tubes (200 μL) and placed in a black microtiter plate (Dynatek Laboratories, Chantilly, Va.). The plates were then read directly using a Fluoroskan II fluorometer (Flow Laboratories, McLean, Va.) using an excitation wavelength of 495 nm and monitoring emission at 520 nm for fluorescein, using an excitation wavelength of 591 nm and monitoring emission at 612 nm for Texas Red, and using an excitation wavelength of 570 nm and monitoring emission at 590 nm for lissamine or TAMRA. The quantity of eluted oligonucleotide was determined by dividing the amount of measured fluorescence (3.84 relative fluorescence units (rfus)) by the specific activity of the Texas Red oligonucleotide (6.9 rfu per μg of oligonucleotide). It was therefore determined that $10^8$ oligonucleotides were present per element in the array.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A spring probe comprising a tubular housing encasing a compression spring, said spring in mechanical communication with a plunger, said plunger having a first region extending out of said housing, said first region comprising a cone-shaped fluted tip terminating as a flat surface, said surface perpendicular to a longitudinal axis of said housing, said cone-shaped tip having in cross-section two exterior sides adjacent said surface which, if said sides extended past said surface, would meet at a point positioned a distance of about 0.00001–0.010 inches beyond said surface.

2. The spring probe of claim 1 where the cone-shaped fluted tip comprises a gold surface.

3. The spring probe of claim 1 wherein said cone-shaped tip has in cross-section two exterior sides adjacent said surface which, if said sides extended past said surface, would meet at a point positioned a distance of about 0.001–0.005 inches beyond said surface.

4. The spring probe of claim 1 wherein said first region comprises a plurality of cone-shaped flutes, the flutes separated by vanes converging toward said flat surface at an angle between approximately 15° and 120°.

5. The spring probe of claim 1 wherein said first region comprises a plurality of cone-shaped flutes, the flutes separated by vanes converging toward said flat surface at an angle between approximately 60° and 90°.

6. A composition comprising a thickening agent at a concentration of about 35 vol % to about 80 vol % based on the total volume of the composition, an oligonucleotide at a concentration ranging from 0.001 µg/mL to 10 µg/mL, and water.

7. The composition of claim 6 wherein the thickening agent is a polyhydric alcohol having at least three hydroxyl groups.

8. The composition of claim 7 wherein the polyhydric alcohol is selected from the group consisting of glycerol, trimethylolpropane, trimethylolethane, pentaerythritol, and saccharides.

9. The composition of claim 8 wherein the saccharide is selected from the group consisting of mannitol, sucrose, fructose, lactose, cellulose and corn syrup.

10. The composition of claim 7 wherein the oligonucleotide is at a concentration of 0.05 µg/mL to 0.5 µg/mL.

11. The composition of claim 6 wherein the thickening agent is glycerol present at a concentration of 40 vol % to 60 vol %.

12. The composition of claim 6 wherein the oligonucleotide is at a concentration ranging from 0.01 µg/mL to 1 µg/mL.

13. The composition of claim 6 wherein the oligonucleotide comprises 15 to 50 nucleotides.

14. The composition of claim 6 wherein the oligonucleotide comprises 50 to 1,000 nucleotides.

15. The composition of claim 6 wherein the oligonucleotide is single stranded.

16. The composition of claim 6 wherein the oligonucleotide is duplex.

17. The composition of claim 6 wherein the oligonucleotide has an amino (—NH$_2$) group at a 5' end of the oligonucleotide.

18. The composition of claim 17 wherein the oligonucleotide has a hexylamine (—(CH$_2$)$_6$—NH$_2$) group at a 5' end of the oligonucleotide.

19. The composition of claim 17 further comprising trichlorotriazine.

20. The composition of claim 6 having a pH of 7 to 9 and further comprising a buffering agent.

21. The composition of claim 20 wherein the buffering agent is selected from the group consisting of sodium phosphate, sodium borate, sodium carbonate and Tris HCl.

22. The composition of claim 6 having a temperature of 18–25° C.

23. The composition of claim 6 having a viscosity at 20° C. of about 6 to 80 centipoise at 25° C.

\* \* \* \* \*

SEQUENCE LISTING

<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Oligonucleotide Produced by
      Solid Phase Synthesis

<400> SEQUENCE: 1
gtcatactcc tgcttgctga tccacatctg                                    30

<210> SEQ ID NO 2
<211> LENGTH: 24
<212> TYPE: DNA
<213> ORGANISM: Artificial Sequence
<220> FEATURE:
<223> OTHER INFORMATION: Oligonucleotide Produced by
      Solid Phase Synthesis

<400> SEQUENCE: 2
tgtggatcag caagcaggag tatg                                          24

<210> SEQ ID NO 3
<211> LENGTH: 38
<212> TYPE: DNA
<213> ORGANISM: Artificial Sequence
<220> FEATURE:
<223> OTHER INFORMATION: Oligonucleotide Produced by
      Solid Phase Synthesis

<400> SEQUENCE: 3
actactgatc aggcgcgcct tttttttttt tttttttt                           38

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide Produced by
      Solid Phase Synthesis

<400> SEQUENCE: 4
catactcctg cttgctgatc caca                                          24

<210> SEQ ID NO 5
<211> LENGTH: 39
<212> TYPE: DNA

-continued

```
<213> ORGANISM: Artificial Sequence
<220> FEATURE:
<223> OTHER INFORMATION: Oligonucleotide Produced by
      Solid Phase Synthesis

<400> SEQUENCE: 5
aaaaaaaaaa aaaaaaaaaa ggcgcgcctg atcagtagt                              39

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide Produced by
      Solid Phase Synthesis

<400> SEQUENCE: 6
cagatgtgga tcagcaagca ggagtatgac                                       30
```